(12) United States Patent
DeSousa

(10) Patent No.: US 7,419,788 B2
(45) Date of Patent: Sep. 2, 2008

(54) METHOD FOR SCREENING ANTI-BACTERIAL AGENTS

(75) Inventor: Sunita Maria DeSousa, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 297 days.

(21) Appl. No.: 10/497,415

(22) PCT Filed: Dec. 3, 2002

(86) PCT No.: PCT/GB02/05534

§ 371 (c)(1),
(2), (4) Date: Sep. 24, 2004

(87) PCT Pub. No.: WO03/048381

PCT Pub. Date: Jun. 12, 2003

(65) Prior Publication Data

US 2005/0032137 A1 Feb. 10, 2005

(30) Foreign Application Priority Data

Dec. 5, 2001 (SE) .................... 0104101

(51) Int. Cl.
*G01N 33/53* (2006.01)
*G01N 33/569* (2006.01)
*C12Q 1/00* (2006.01)

(52) U.S. Cl. .............. 435/7.1; 435/4; 435/6; 435/7.32; 435/7.9; 435/7.92

(58) Field of Classification Search ............ 435/4, 435/6, 7.1, 7.2, 7.32, 7.9, 7.92
See application file for complete search history.

(56) References Cited

U.S. PATENT DOCUMENTS 4,568,649 A 2/1986 Bertoglio-Matte

FOREIGN PATENT DOCUMENTS

| EP | 0 154 734 | 8/1990 |
|---|---|---|
| EP | 0 378 059 | 9/1993 |
| WO | WO-96/16082 | 5/1996 |
| WO | WO-99/38958 | 8/1999 |
| WO | WO-99/60155 | 11/1999 |
| WO | WO-00/10587 | 3/2000 |
| WO | WO-00/52035 | 9/2000 |
| WO | WO-01/12142 | 2/2001 |
| WO | WO-01/94622 | 12/2001 |
| WO | WO-01/94623 | 12/2001 |

OTHER PUBLICATIONS

Barbosa, M.D.F., et al., "Development of a Pathway Assay to Screen for Bacterial Cell Wall Biosynthesis Inhibitors," 41:248 (2001) XP009010101.

Boyle, D.S., et al., "mraY Is an Essential Gene for Cell Growth in *Escherichia coli*," Journal of Bacteriology, 180(23):6429-6432 (1998).

Branstrom, A.A., et al., "In situ assay for identifying inhibitors of bacterial transglycosylase," FEMS Microbiology Letters, 191:187-190 (2000).

Chandrakala, B., et al., "Novel Scintillation Proximity Assay for Measuring Membrane-Associated Steps of Peptidoglycan Biosynthesis in *Escherichia coli*," Antimicrobial Agents and Chemotherapy, 45(3):768-775 (2001).

den Blaauwen, T., et al., "Interaction of Monoclonal Antibodies with the Enzymatic Domains of Penicillin-Binding Protein 1b of *Escherichia coli*," Journal of Bacteriology, 172(1):63-70 (1990).

Denome, S.A., et al., "*Escherichia coli* Mutants Lacking All Possible Combinations of Eight Penicillin Binding Proteins: Viability, Characteristics, and Implications for Peptidoglycan Synthesis," Journal of Bacteriology, 181(13):3981-3993 (1999).

Ge, M., et al., "Vancomycin Derivatives That Inhibit Peptidoglycan Biosynthesis Without Binding D-Ala-D-Ala," Science, 284:507-511 (1999).

Goldman, R.C., et al., "Chlorobiphenyl-desleucyl-vancomycin inhibits the transglycosylation process required for peptidoglycan synthesis in bacteria in the absence of dipeptide binding," FEMS Microbiology Letters, 183:209-214 (2000).

Lefevre, F., "Topographical and Functional Investigation of *Escherichia coli* Penicillin-Binding Protein 1b by Alanine Stretch Scanning Mutagenesis," Journal of Bacteriology, 179(15):4761-4767 (1997).

Lo, M.C., et al., "A New Mechanism of Action Proposed for Ramoplanin," J. Am. Chem. Soc., 122:3540-3541 (2000).

Mengin-Lecreuix, D., et al., "The murG Gene of *Escherichia coli* Codes for the UDP-N-Acetylglucosamine:N-Acetylmuramyl-(Pentapeptide) Pyrophosphoryl-Undecaprenol N-Acetylglucosamine Transferase Involved in the Membrane Steps of Peptidoglycan Synthesis," 173(15):4625-4636 (1991).

Pinho, M.G., et al., "An acquired and a native penicillin-binding protein cooperate in building the cell wall of drug-resistant staphylococci," PNAS, 98(19):10886-10891 (2001).

Tamura, T., et al., "On the process of cellular division in *Escherichia coli*: Isolation and characterization of penicillin-binding proteins 1a, 1b, and 3," Proc. Natl. Acad. Sci. USA, 77(8):4499-4503 (1980).

van Heijenoort, Y., et al., "Membrane Intermediates in the Peptidoglycan Metabolism of *Escherichia coli*: Possible Roles of PBP 1b of PBP 3," Journal of Bacteriology, 174(11):3549-3557 (1992).

Yousif, S.Y., "Lysis of *Escherichia coli* by β-Lactam Antibiotics: Deletion Analysis of the Role of Penicillin-binding Proteins 1A and 1B," Journal of General Microbiology, 131:2839-2845 (1985).

(Continued)

*Primary Examiner*—Rodney P Swartz

(57) ABSTRACT

The invention provides a method of screening for potential anti-bacterial agents being antagonists of the transpeptidase enzyme involved in peptidoglycan biosynthesis in bacteria. The method is suitable for high throughput screening of compounds.

9 Claims, No Drawings

METHOD FOR SCREENING ANTI-BACTERIAL AGENTS

CROSS-REFERENCE TO RELATED APPLICATIONS

This application is a national stage filing under U.S.C. 371 of International Application No. PCT/GB02/05534, filed Dec. 3, 2002, which claims priority from Swedish Application No. 0104101-1, filed Dec. 5, 2001, the specification of which is incorporated by reference herein. International Application No. PCT/GB02/05534 was published under PCT Article 21(2) in English.

The present invention relates to a method of screening for potential anti-bacterial agents.

Peptidoglycan is a major component of the bacterial cell wall that gives the wall its shape and strength. It is unique to bacteria and is found in all bacteria, both gram-positive and gram-negative. Peptidoglycan is a polymer of glycan strands that are cross-linked through short peptide bridges. It consists of alternating β1-4 linked residues of N-acetyl glucosamine (GlcNAc) and N-acetyl muramic acid (MurNAc). A pentapeptide chain is attached to MurNAc (MurNAc-pentapeptide) and cross-linking occurs between these peptide chains.

Biosynthesis of peptidoglycan can be divided into three stages: firstly, synthesis of the precursors in the cytoplasm, secondly, transfer of the precursors to a lipid carrier molecule and, thirdly, insertion of the precursors into the cell wall and coupling to existing peptidoglycan.

The precursors synthesized in the cytoplasm are the sugar nucleotides: UDP-N-acetyl-glucosamine (UDP-GlcNAc) and UDP-N-acetylmuramylpentapeptide (UDP-MurNAc-pentapeptide).

The second stage, which occurs in the cytoplasmic membrane, is catalyzed by two enzymes and involves synthesis of a disaccharide unit on a lipid carrier, undecaprenyl phosphate. The lipid carrier is also involved in the synthesis of other components of the bacterial cell wall.

The first enzyme catalyses the transfer of phosphoryl-N-acetyl muramyl pentapeptide from UDP-MurNAc-pentapeptide to undecaprenyl phosphate with the simultaneous release of UMP. This enzyme is called phospho-N-acetylmuramyl-pentapeptide translocase (hereafter referred to as "the translocase") and is the product of the gene mraY in Escherichia coli. The product, undecaprenyl-pyrophosphate-N-acetyl-muramylpentapeptide (Lipid-P-P-MurNAc-pentapeptide) or Lipid I or Lipid linked precursor I is the substrate for the second enzyme.

N-acetylglucosaminyl transferase, transfers N-acetylglucosamine from UDP-GlcNAc (with simultaneous release of UDP) to form undecaprenyl-pyrophosphoryl-N-acetylmuramylpentapeptide-N-acetylglucosamine or Lipid II or Lipid linked precursor II. This enzyme is also called UDP-N-acetylglucosamine: N-acetylmuramyl(pentapeptide)-P-P-undecaprenyl-N-acetylglucosamine transferase (hereafter referred to as "the transferase"). The enzyme is the product of the gene murG in Escherichia coli.

The translocase and the transferase enzymes are essential for bacterial viability (see respectively D. S. Boyle and W. D. Donachie, J. Bacteriol., (1998), 180, 6429-6432 and D. Mengin-Lecreulx, L. Texier, M. Rousseaue and Y. Van Heijenoort, J. Bacteriol., (1991), 173, 4625-4636).

In the third stage, at the exterior of the cytoplasmic membrane, polymerization of the glycan occurs. The disaccharide-pentapeptide unit is transferred from the lipid carrier to an existing disaccharide unit or polymer by a peptidoglycan transglycosylase (also referred to as a peptidoglycan polymerase) (hereafter referred to as "the transglycosylase"). The joining of the peptide bridge is catalyzed by peptidoglycan transpeptidase (hereafter referred to as "the transpeptidase"). Both enzyme activities which are essential reside in the same molecule, the penicillin binding proteins (or PBPs), as in PBP 1a or 1b in Escherichia coli. These are the products of the ponA and ponB genes respectively, in Escherichia coli.

There are several PBPs in the bacterial cell and these can be divided into two classes, the low molecular mass (LMM) and high molecular mass (HMM) PBPs. Some of the HMM PBPs are bifunctional enzymes having both transpeptidase and transglycosylase activity. Of the HMM PBPs, PBP2 and PBP3 and either PBP1A or PBP1B of E. coli have been shown to be essential for cell viability. The LMM PBPs appear to be important but not essential for cell growth (e.g. PBPs 4, 5, 6 of E. coli can be deleted resulting in growth defects but the cell survives, see S. A. Denome, P. K. Elf, T. A. Henderson, D. E. Nelson and K. D. Young, J. Bacteriol., (1999), 181(13), 3981-3993).

On transfer of the disaccharide-pentapeptide unit from the lipid precursor to an existing peptidoglycan chain the lipid is released as a molecule of undecaprenyl pyrophosphate. This has to be cleaved by a bacitracin-sensitive undecaprenyl pyrophosphorylase, also called undecaprenyl pyrophosphorylase or C55-isoprenyl pyrophosphorylase (hereafter referred to as the "lipid pyrophosphorylase") to generate undecaprenyl phosphate which can then re-enter the cycle at the second stage.

Both the transglycosylase and the transpeptidase enzymes (which reside within the high molecular weight penicillin binding proteins or PBPs) represent prime targets for drug discovery that have not been fully exploited due to the lack of suitable assays amenable to high throughput screening. Two antibiotics target these proteins: the glycopeptides and the beta-lactam antibiotics-penicillins and cephalosporins. The beta-lactam antibiotics, which inhibit the transpeptidase, are one of the most successful and have yielded many generations of drugs. Vancomycin, a glycopeptide, is an inhibitor of the transglycosylase and in many cases of drug resistance is the last resort for treatment of bacterial infections. It is thus thought that new inhibitors of the transglycosylase and transpeptidase will be as successful and could become clinically useful antibiotics.

The transpeptidase enzyme has traditionally been hard to assay. Due to transpeptidase activity, a cross-link is typically formed between the fourth amino acid, D-alanine, of one peptide chain and the third amino acid e.g. diaminopimelic acid (or L-lysine in some bacteria) of an adjacent peptide chain. The true test for inhibition of transpeptidation is to analyze the peptidoglycan formed for the degree of cross-linking which is a very laborious test; in the presence of a transpeptidase inhibitor the degree of cross-linking is reduced.

During formation of the peptide cross-link the fifth amino acid, D-alanine, is released. There is known in the art an indirect assay for the transpeptidase that monitors release of D-alanine. However, since the same reaction can also happen with a carboxypeptidase (that cleaves the D-alanine without forming a peptide cross-link), transpeptidase activity is measured as D-alanine release that is dependent on the presence of UDP-MurNAc and UDP-GlcNAc in the assay. This requires that release of the D-alanine occurs concomitantly with synthesis & cross-linking of the peptidoglycan; the carboxypeptidase activity should be independent of synthesis and the presence of UDP-GlcNAc in particular.

Another method known for assaying the transpeptidase relies on cleavage of a colored β-lactam, e.g. nitrocefin. The β-lactam antibiotics covalently bind to an active site serine residue in the transpeptidase, thereby inactivating the enzyme activity. The β-lactam ring is hydrolyzed in this process and if one uses a β-lactam like nitrocefin the hydrolysis can be monitored colorimetrically. This method is not very sensitive as a measure of transpeptidase activity, although it is widely used to study the activity of β-lactamases.

The easiest known method for the detection of inhibitors of the transpeptidase is by competition (by a test compound) for the binding of a labelled (e.g. radioactive or fluorescent) β-lactam to a penicillin binding protein. This has been most frequently used to screen for new inhibitors. Because of the nature of the assay most inhibitors picked up in this screen are new β-lactams that act by the same mechanism, that is, by covalently binding to the active site serine residue of the transpeptidase. Since bacteria have developed resistance to the β-lactam antibiotics, which is due to the presence of enzymes (β-lactamases) that hydrolyse the β-lactams, it is desirable to find transpeptidase inhibitors that are not β-lactams.

In accordance with the present invention, there is therefore provided a method of screening for potential anti-bacterial agents which comprises:

(1) providing a membrane preparation obtained from a bacterial strain, wherein the membrane preparation is deficient for peptidoglycan transpeptidase activity;

(2) preparing a reaction mixture comprising the membrane preparation, a UDP-N-acetylmuramylpentapeptide (UDP-MurNAc-pentapeptide), radiolabelled UDP-N-acetyl glucosamine (UDP-GlcNAc) and a source of divalent metal ions;

(3) incubating the reaction mixture for a defined period under conditions suitable for uncross-linked peptidoglycan synthesis to occur;

(4) adding to the reaction mixture of step (3),
   (a) a source of peptidoglycan transpeptidase, to allow the synthesis of cross-linked peptidoglycan, and
   (b) a test compound;

(5) after a defined period, adding to the reaction mixture of step (4) a fluorescer supported by, in or on a suitable substrate, and a detergent; and (6) measuring light energy emitted by the fluorescer which is indicative of the presence of radiolabelled cross-linked peptidoglycan.

In the context of the present specification, it should be understood that the abbreviation "UDP" refers to uridine (5'-)diphosphate.

The method according to the present invention is very conveniently carried out using 96-well microtitre plates, thereby enabling a fast, simple and reproducible way of measuring enzyme activity.

The bacterial membranes may be prepared as described in Example 1 of WO 99/60155. The membranes represent a source of translocase, transferase, transglycosylase, lipid pyrophosphorylase and undecaprenyl phosphate which are necessary to make uncross-linked peptidoglycan. However, the membranes are deficient for peptidoglycan transpeptidase activity. This may be achieved, for example, by contacting the bacterial membranes with an inhibitor of peptidoglycan transpeptidase (e.g. ampicillin) or by using the membranes of a mutant bacterial strain in which peptidoglycan transpeptidase is inactivated by mutation (e.g. a point mutation or deletion mutation).

The quantity of membranes used will typically be in the range from 1 to 20 μg, particularly from 4 to 6 μg, protein per well of the microtitre plate.

In one embodiment of the invention, the membranes of *Escherichia coli* bacteria are used. Examples of *E. coli* strains that may be used include AMA1004. Additionally, use can be made of the *E. coli* strain AMA1004 ΔponB::Spc$^r$ when transformed with an expression vector (e.g. a plasmid) comprising a homologous or heterologous gene encoding a penicillin binding protein which is deficient for peptidoglycan transpeptidase activity but which has peptidoglycan transglycosylase activity.

The UDP-MurNAc-pentapeptide used may be any of those usually present in naturally-occurring peptidoglycans and is conveniently purified from bacteria or made enzymatically with precursors from bacteria, e.g. by methods similar to that described by T. den Blaauwen, M. Aarsman and N. Nanninga, J. Bacteriol., (1990), 172, 63-70).

In one embodiment of the invention, the UDP-MurNAc-pentapeptide used is UDP-MurNAc-L-alanine-γ-D-glutamic acid-m-diaminopimelic acid-D-alanine-D-alanine from *Bacillus cereus*.

The concentration of UDP-MurNAc-pentapeptide used per well of microtitre plate will typically be in the range from 5 μM to 300 μM, for example, from 5 μM, 10 μM, 15 μM, 20 μM or 25 μM up to and including 50 μM, 75 μM, 100 μM, 150 μM, 200 μM or 250 μM per well of the microtitre plate.

As radiolabelled UDP-N-acetyl glucosamine, it is convenient to use tritiated UDP-N-acetyl glucosamine (UDP-[$^3$H] GlcNAc, commercially available from NEN-Dupont), at a concentration, for example, in the range from 0.25 μM, 0.5 μM, 1.0 μM, 2.5 μM, 4.2 μM or 5 μM up to and including 10 μM, 12.5 μM, 15 μM, 20 μM or 25 μM per well of the microtitre plate. Concentrations of radiolabelled UDP-N-acetyl glucosamine of 4.2 μM (with 0.6 to 1.2 μCi per well) have been advantageously used.

The divalent metal ions used are preferably magnesium ions. A suitable source of magnesium ions is magnesium chloride, for example at a concentration in the range from 5 to 30 mM, particularly from 10 to 25 mM, per well of microtitre plate.

In step (2) of the method, it may be convenient to use an aqueous medium such as a buffer solution, e.g. of HEPES-ammonia, HEPES-KOH (HEPES being N-[2-hydroxyethyl] piperazine-N'-[2-ethanesulfonic acid]) or Tris[hydroxymethyl]aminomethane hydrochloride ("Tris-HCl"), the buffer solution having a pH of about 7.5. HEPES and Tris-HCl are commercially available from the Sigma-Aldrich Company Limited.

The reaction mixture prepared in step (2) is incubated in step (3) at a temperature in the range from, for example, 20° C. to 37° C. for a period in the range from, for example, 2, 3, 4, 5, 10, 20, 30, 40 or 50 minutes up to and including 100, 110, 120, 130, 140 or 150 minutes, under conditions suitable for enzyme-catalyzed uncross-linked peptidoglycan synthesis to occur.

In step (4) of the invention, a source of peptidoglycan transpeptidase is added to allow the synthesis of cross-linked peptidoglycan. Also, in step (4), a test compound having potential antibacterial properties is added, typically in an aqueous solution of dimethyl sulphoxide.

The reaction mixture of step (4) is incubated for a further period at a temperature in the range from, for example, 20° C. to 37° C. The incubation period will normally be shorter than the incubation period for the reaction mixture of step (3), e.g. in the range from 1, 5, 10 or 15 minutes up to and including 20, 25 or 30 minutes.

Once the incubation period has come to an end, any further reaction is terminated upon addition in step (5) of the fluorescer supported by, in or on a suitable substrate and the detergent to the reaction mixture.

The detergent is any agent that is capable of emulsifying oil and/or acts as a wetting agent or surfactant. Examples of detergents that may be used include Triton X-100 (t-octylphenoxypolyethoxyethanol), Tween 20 (polyoxyethylenesorbitan monolaurate), Tween 80 (polyoxyethylenesorbitan monooleate), octyl-β-glycoside, CHAPS (3-[(3-cholamidopropyl)dimethylammonio]-1-propane-sulphonate), Brij-35 (polyoxyethylene lauryl ether) and Sarkosyl (sodium lauryl sarcosinate).

The fluorescer used may be any of those routinely employed in scintillation proximity assays. The fluorescer is associated with or supported by, in or on a substrate, for example, lectin-coated beads, RNA-binding beads, antimouse antibody coated PVT (polyvinyltoluene) beads or wheatgerm agglutinin-coated PVT beads, all of which beads are commercially available from Amersham Inc. The substrate (e.g. beads) chosen should be capable of binding to bacterial cell walls.

In one embodiment of the invention, lectin-coated beads (particularly wheatgerm agglutinin-coated beads) impregnated with a fluorescer are used, for example, as described in U.S. Pat. No. 4,568,649 and European Patent No. 154,734. The beads (known as "Scintillation Proximity Assay" (or SPA) beads) are commercially available from Amersham Inc.

The beads (with fluorescer), which are conveniently added in the form of an aqueous suspension, are contacted with the reaction mixture of step (4) for a period of at least 10 minutes, preferably 3 to 10 hours or more (e.g. overnight), before the plate is "counted" in step (6), e.g., in a "Microbeta Tilux" counter.

Without being bound to any particular theory, it is believed that through the binding of the substrate to bacterial cell wall material (e.g. wheatgerm agglutinin-coated SPA beads are capable of binding sugar molecules, specifically N-acetyl glucosamine, present in bacterial cell wall material), radiolabelled crosslinked peptidoglycan formed in step (4) is brought into close proximity with the fluorescer which becomes activated by the radiation energy, resulting in the emission of light energy which is measured in step (6). Thus, light emitted from the fluorescer is believed to be indicative of the formation of cross-linked peptidoglycan.

The present invention will now be further explained by reference to the following illustrative examples in which the abbreviation HEPES refers to N-[2-hydroxyethyl]piperazine-N'-[2-ethanesulfonic acid].

EXAMPLE 1

(i) Formation of Radiolabelled Uncross-linked Peptidoglycan 4 mg of *Escherichia coli* AMA1004 cell membranes prepared as described in WO 99/60155 were incubated with 5 ml of 100 mM ampicillin in 50 mM Tris HCl buffer pH 7.5 and 0.1 mM $MgCl_2$ for 30 minutes at room temperature. The membranes were sedimented by centrifugation at 150,000×g for 15 minutes and then washed three times. They were finally resuspended in 1 ml of 50 mM Tris HCl buffer and 0.1 mM $MgCl_2$.

The wells of a microtitre plate were individually filled with 15 µl of a solution containing 5 µg of *Escherichia coli* AMA1004 cell membranes treated with ampicillin as described above (the membranes provided a source of translocase, transferase, transglycosylase, lipid pyrophosphorylase and undecaprenyl phosphate), 15 µM UDP-MurNAc-L-alanine-γ-D-glutamic acid-m-diaminopimelic acid-D-alanine-D-alanine, 4.2 µM tritiated UDP-N-acetyl glucosamine (0.6 µCi-1.2 µCi per well), 50 mM HEPES-ammonia buffer pH 7.5, and 10 mM magnesium chloride ($MgCl_2$). The microtitre plate was incubated at 37° C. for 120 minutes.

(ii) Formation of Radiolabelled Cross-linked Peptidoglycan

To each well was then added 10 µl containing 50 mM HEPES-ammonia buffer pH 7.5, 10 mM $MgCl_2$, UDP-N-acetyl glucosamine to a final concentration (in 25 µl) of 250 µM, an extract containing PBP1b (a source of transpeptidase enzyme) obtained from the membranes of *Escherichia coli* AMA1004 ΔponA; pBS96, and 2 µl of test compound (penicillin G, a known transpeptidase inhibitor) in dimethyl sulphoxide (DMSO).

In *Escherichia coli* AMA1004 ΔponA; pBS96, the ponA gene encoding PBP1a is inactivated and the ponB gene encoding PBP1b is overexpressed since the strain contains a plasmid comprising a further copy of ponB under the control of its native promoter.

The membranes of this *E. coli* strain were prepared as described in WO 99/60155. They were then treated with a detergent, 1% (3-[(3-cholamidopropyl)dimethylammonio]-1-propane-sulphonate, (CHAPS), and 1M NaCl at a protein concentration of 5 mg/ml for 1 hour at room temperature. The mixture was then centrifuged at 150,000×g for 15 minutes in a Beckman table top ultracentrifuge and the supernatant containing PBP1b collected. The quantity of PBP1b protein used was the "soluble fraction" equivalent to 5 µg of starting membrane.

The microtitre plate was incubated at 37° C. for 15 minutes and thereafter 75 µl of 6 mM ethylenediaminetetraacetic acid (EDTA) was added.

(iii) Detecting Radiolabelled Cross-linked Peptidoglycan

Following addition of the EDTA, there was added to each well 100 µl of an aqueous suspension of wheatgerm agglutinin-coated scintillation proximity assay beads comprising 500 µg beads in a solution of 50 mM HEPES-ammonia buffer pH 7.5 containing 0.4% "Sarkosyl" detergent (sodium lauryl sarcosinate) so that the final concentration of "Sarkosyl" detergent (in 200 □1) was 0.2%.

The microtitre plate was left for 3 to 10 hours at room temperature before being counted in the "Microbeta Trilux" counter.

Four wells of the microtitre plate were used as controls: two wells contained no extract containing PBP1b (0% reaction controls) and a further two wells contained no test compound (100% reaction controls).

Table 1 below enumerates the inhibitory effects of penicillin G on the transpeptidase enzyme (after subtracting the corresponding 0% reaction readings).

TABLE 1

| Test Compound | Counts per minute | % Inhibition |
| --- | --- | --- |
| — | 5296 | 0 |
| Penicillin G | 319 | 94 |

EXAMPLE 2

In this Example, the method described in Example 1 is repeated except that in (i) the membranes used are those of

*Escherichia coli* AMA1004 ΔponB::Spc$^r$, a mutant from which the gene ponB encoding PBP1b has been inactivated, as described by S. Y. Yousif, J. K. Broome-Smith and B. G. Spratt, *J. Gen. Microbiol.*, (1985), 131, 2839-2845. The mutant is transformed with a plasmid expressing PBP1b that has a Ser510Ala mutation. This is the active site serine that the β-lactams covalently bind to. Thus, the membranes lack transpeptidase activity and there is no need therefore to treat the membranes with ampicillin.

What is claimed is:

1. A method of screening for potential anti-bacterial agents which comprises:
   (1) providing a membrane preparation obtained from a bacterial strain, wherein the membrane preparation is deficient for peptidoglycan transpeptidase activity;
   (2) preparing a reaction mixture comprising the membrane preparation, a UDP-N-acetylmuramylpentapeptide, radiolabelled UDP-N-acetyl glucosamine and a source of divalent metal ions;
   (3) incubating the reaction mixture for a defined period under conditions suitable for uncross-linked peptidoglycan synthesis to occur;
   (4) adding to the reaction mixture of step (3),
      (a) a source of peptidoglycan transpeptidase, to allow the synthesis of cross-linked peptidoglycan, and
      (b) a test compound;
   (5) contacting the reaction mixture of step (4) with a fluorescer supported by, in or on a suitable substrate, and a detergent for a period of at least 10 minutes; and
   (6) measuring light energy emitted by the fluorescer which is indicative of the presence of radiolabelled cross-linked peptidoglycan, wherein a decrease in flourescence compared to a control indicates that the test compound is a potential anti-bacterial agent.

2. A method according to claim 1, wherein the UDP-N-acetylmuramylpentapeptide is UDP-MurNAc-L-alanine-γ-D-glutamic acid-m-diaminopimelic acid-D-alanine-D-alanine.

3. A method according to claim 1 or claim 2, wherein the source of divalent metal ions is magnesium chloride.

4. A method according to any one of claims 1 to 3, wherein the bacterial strain is a strain of *Escherichia coil*.

5. A method according to claim 4, wherein the *Escherichia coil* strain is AMA 1004 and wherein the membrane preparation obtained therefrom is contacted with an inhibitor of peptidoglycan transpeptidase.

6. A method according to claim 4, wherein the *Escherichia coil* strain is AMA 1004 ΔponB::Spc$^r$ transformed with an expression vector comprising a homologous or heterologous gene encoding a penicillin binding protein deficient for peptidoglycan transpeptidase activity.

7. A method according to any one of claims 1 to 6, wherein the fluorescer is supported by, in or on lectin-coated beads.

8. A method according to any one of claims 1 to 7, wherein the detergent is selected from Triton X-100 and Sarkosyl.

9. A method according to any one of claims 1 to 8, wherein the test compound is an antagonist of the transpeptidase.

* * * * *